(12) United States Patent
Hickling

(10) Patent No.: US 10,179,075 B1
(45) Date of Patent: Jan. 15, 2019

(54) SHOULDER THERMAL THERAPY WRAP

(76) Inventor: Shawn Hickling, Cypress, CA (US)

(*) Notice: Subject to any disclaimer, the term of this patent is extended or adjusted under 35 U.S.C. 154(b) by 1096 days.

(21) Appl. No.: 12/798,669

(22) Filed: Apr. 7, 2010

(51) Int. Cl.
*A61F 5/00* (2006.01)
*A61F 13/04* (2006.01)

(52) U.S. Cl.
CPC .................... *A61F 13/046* (2013.01)

(58) Field of Classification Search
CPC ............. A61F 13/046; A61F 13/146; A61F 2007/0029; A61F 2007/0001; A61F 2007/003; A61F 7/02; A61F 7/10; A61F 2007/0031; A61F 2007/108; A61F 5/05816; A61F 5/0118; A61F 5/013; A61F 5/05858
USPC ............ 602/14, 20, 2, 62, 63, 61, 4, 19, 5; 128/878, 845, 846, 869; 2/45, 44; 607/108, 112
See application file for complete search history.

(56) References Cited

U.S. PATENT DOCUMENTS

| 4,591,703 | A | | 5/1986 | Kuo | |
|---|---|---|---|---|---|
| 4,598,703 | A | * | 7/1986 | Lindemann | ............ 602/4 |
| 4,915,102 | A | * | 4/1990 | Kwiatek et al. | ......... 604/307 |
| 4,931,333 | A | | 6/1990 | Henry | |
| 5,148,804 | A | * | 9/1992 | Hill et al. | .......... 607/108 |
| 5,743,867 | A | | 4/1998 | Hickling | |
| 6,083,256 | A | * | 7/2000 | Der Ovanesian | ........ 607/114 |
| 6,398,746 | B2 | * | 6/2002 | Bramlage et al. | ............ 602/5 |
| D473,656 | S | | 4/2003 | Miros et al. | |
| 6,945,988 | B1 | * | 9/2005 | Jones | .......... 607/108 |
| D527,103 | S | | 8/2006 | Nahavandi | |
| D532,523 | S | | 11/2006 | Krahner et al. | |
| 2008/0188788 | A1 | | 8/2008 | Serola | |
| 2010/0198324 | A1 | * | 8/2010 | Graaham, Jr. | ........ A61F 7/02 607/112 |
| 2010/0210985 | A1 | * | 8/2010 | Kuorak et al. | ........... 602/20 |

OTHER PUBLICATIONS

"Bio Rubber," Apr. 30, 2006, Yamamoto Corporation, accessed May 1, 2012, <http://web.archive.org/web/20060430023300/http://www.yamamoto-bio.com/yamamoto_e/medical.html>.*

* cited by examiner

Primary Examiner — Victoria J Hicks
(74) Attorney, Agent, or Firm — Thomas M. Freiburger

(57) ABSTRACT

A heat/cold therapy wrap for the shoulder envelops the shoulder, over the clavicle and down over a portion of the upper arm. Compression against the shoulder is adjustable via a torso strap and a separate compression strap. A pair of pockets receive thermal gel material, preferably a non-migrating gel which will easily form to the contours of the shoulder and will remain as an integral plastic mass, not migrating within the enveloping bag under pressure. The ergonomically designed shoulder wrap is light in weight and engages the shoulder in a way that allows range of motion exercises in which heat/ice therapy combined with motion are useful to treat frozen shoulder syndromes or adhesive capsulitis. In one embodiment of the wrap an arm cuff is provided at the lower end of the device to encircle the upper arm. Another embodiment has no permanent arm cuff but has a versatile compression strap.

14 Claims, 8 Drawing Sheets

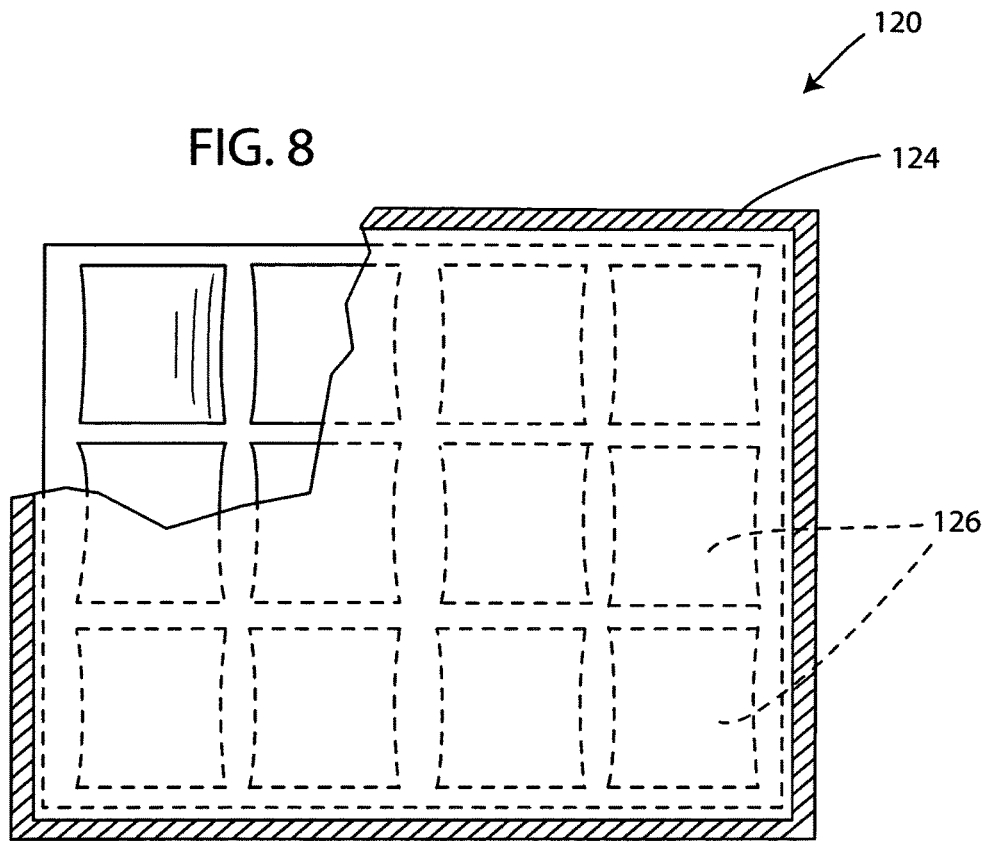
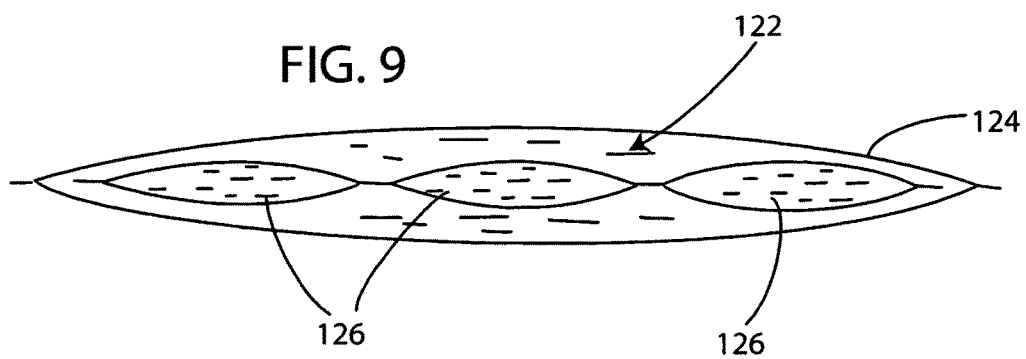

SHOULDER THERMAL THERAPY WRAP

BACKGROUND OF THE INVENTION

This invention concerns thermal therapy for treatment of injuries to the shoulder, and particularly a shoulder strap holding heat or cold packs and effective to apply compression to areas of the shoulder as needed, while also being lightweight, pliable and flexible to allow for movement as needed.

A basic understanding of the anatomy and kinesiology of the shoulder complex is useful in understanding the design and application of the shoulder wrap of the invention. See, for example, U.S. Pat. Nos. 4,591,703 and 6,398,746, the disclosures of which are incorporated herein by reference.

It is known that cooling and heating are useful therapeutic treatments for soft tissue trauma; normally cooling is applied immediately following an injury, and heating is often applied as subsequent therapy for healing the injury. The application of these thermal treatments along with compressive support of the shoulder joint, while allowing substantially full movement, are objectives of the present invention.

Thermal treatment of the shoulder is focused on treatment of the soft tissue associated with the joint, including the rotator cuff and the bursa.

U.S. Pat. No. 5,743,867, commonly owned with this application, discloses a therapeutic wrapping for a joint, particularly the ankle. This wrapping includes a system for retaining thermal treatment pads on the interior of the wrap to provide thermal treatment and joint support. To accommodate its intended purpose as an ankle wrapping, the structure includes an opening to accommodate the protruding calcaneus or heel bone. This wrap is specifically suited for treating the ankle and not the shoulder because the differing joint structures require treatment at different positions. With the ankle, considerable restraint of movement is acceptable and even desirable, while with the shoulder it is preferred to maintain as much as possible of normal range of motion during treatment.

U.S. Pat. No. 6,945,988 describes a shoulder joint cooling device that includes a collection of cooling pads to be draped over the shoulder and held in place by gravity, a neck strap and an upper arm segment that wraps around the user's upper arm. The device does not provide cooling of the entire shoulder, and specifically lacks cooling in the important rotator cuff area that is commonly subject to trauma. This device does not provide compressive support, and heat trauma is not envisaged.

U.S. design Pat. No. 473,656 discloses a shoulder wrap for applying cooling and compression. While this wrap apparently extends over the entire shoulder, it is not clear from the disclosure where on the shoulder or how the cooling is applied, although there appears to be a hose attached to the wrap. Likewise, it is not apparent from this document how or where this wrap applies compression. There are two straps, a broad strap which appears to be a torso encircling strap, and a narrower strap that appears to be a sling for supporting the lower arm. This interpretation is consistent with information given on the assignee's web site; see intl.gameready.com/products/shoulder.htm. There appears to be no consideration given to freedom of shoulder movement during treatment. On the contrary, the use of a sling implies a desire to immobilize the shoulder. Heat treatment is apparently not considered.

U.S. design Pat. 527,108 and 532,523 disclose thermal therapy pads which are elaborate, complex devices apparently connected in use to an external source of circulating heat transfer fluid. The pad of No. 532,523 includes an integral arm sling. Neither of these pads apparently provides compressive support. The device of No. 532,523 is evidently intended to immobilize the shoulder when in use.

SUMMARY OF THE INVENTION

A heat/cold therapy wrap for the shoulder, in accordance with the invention, envelops the shoulder, over the clavicle and down over a portion of the upper arm. Compression against the shoulder is adjustable via a torso strap and a separate under the arm compression strap. On the inside surface of the main panel that wraps over the shoulder are a pair of pockets that receive thermal gel material, preferably a non-migrating gel which will easily form to the contours of the shoulder and will remain as an integral plastic mass that will not migrate within the enveloping bag under pressure and gravity. The ergonomically designed shoulder wrap is light in weight and engages the shoulder in a way that allows range of motion exercises in which heat/ice therapy combined with motion are useful to treat frozen shoulder syndromes or adhesive capsulitis.

For minimal weight and increased flexibility the material BIO RUBBER (Yamamoto Corporation of Osaka, Japan) preferably is used. The main panel formed of this material can be only 2 mils in thickness. Comfort and flexibility are improved.

In one embodiment of the wrap an arm cuff is provided at the lower end of the device to encircle the upper arm. This is tightened using the separate compression strap described above. In another embodiment, the arm cuff is not included, but the embodiment has a removable compression strap that can be placed, via hook and loop fasteners, in different positions as desired for treating the particular patient's injury. The combination of the compression strap and the chest or torso strap is effective to deliver compression fully to all important areas in a versatile arrangement, thus assuring the heat or cold is applied effectively.

Another aspect of the invention is embodied in the thermal gel packs themselves. As noted above, the gel in the packs is non-migrating, remaining as a cohesive mass, soft and with elastic properties so as to conform better than ice or previous gel packs. The cohesive nature of the gel, even once subjected to uneven pressures in different areas of the pack, allows more compression to be applied to the affected areas. This cohesiveness also assists in cryokinetics, in which application of cold to the joint is combined with movement of the joint. The gel pack is glycerin based, and in one form the gel will stay cold up to four hours of use. These glycerin-based gels are made of components that differ strongly from typical prior gels.

It is therefore among the objects of the invention to improve over existing thermal shoulder wraps, in the areas of comfort, flexibility, weight and application of desired pressure to affected areas. This object is aided by particular glycerin-based gel formulas providing for non-migrating, cohesive and elastic properties. These and other objects, advantages and features of the invention will be apparent from the following description of a preferred embodiment, considered along with the accompanying drawings.

DESCRIPTION OF THE DRAWINGS

FIGS. 8 and 9 are plan and profile sectional views showing a gel pack of the invention

DESCRIPTION OF PREFERRED EMBODIMENTS

Figure 1:
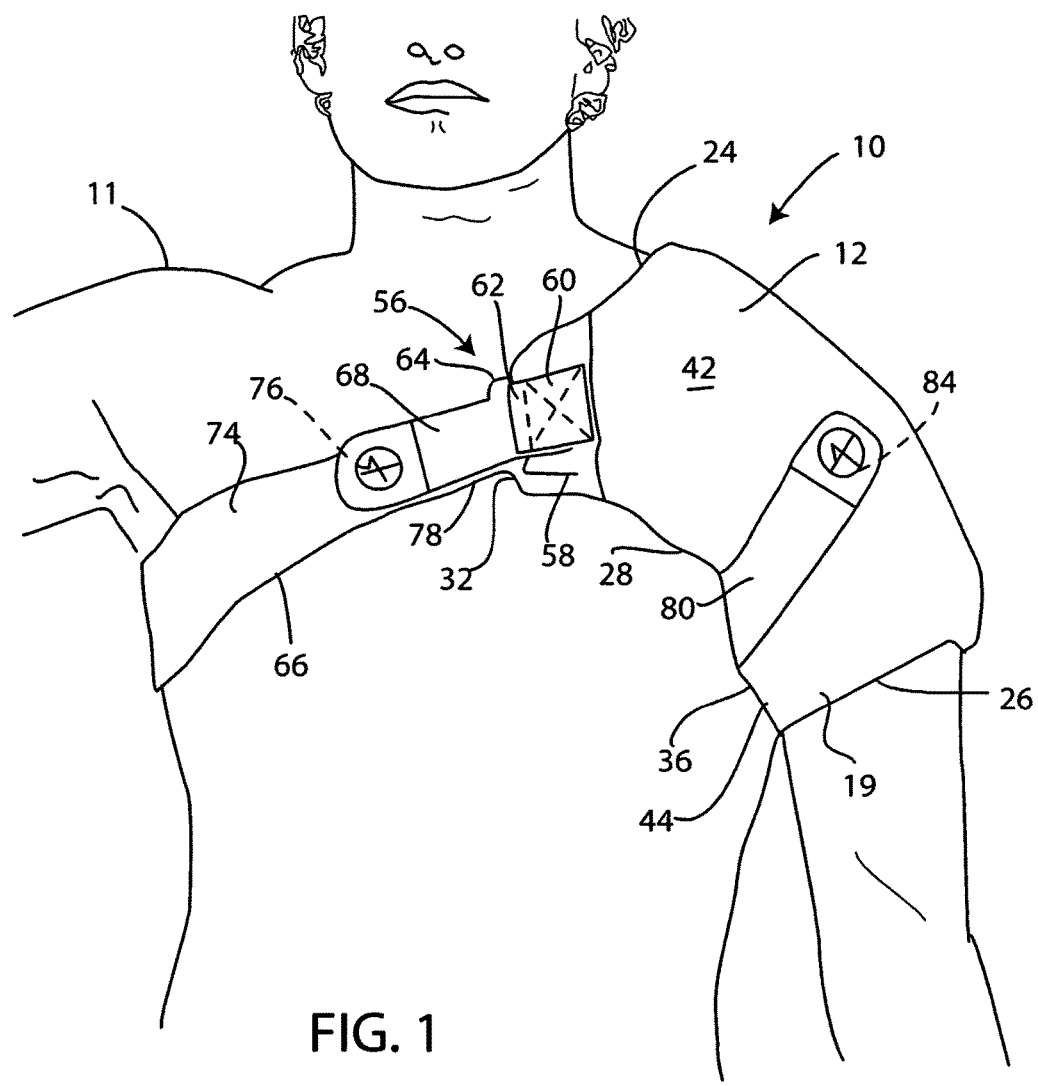
FIG. 1 is a front view showing the shoulder wrap of the invention applied to a shoulder of a person for thermal/compression therapy.
Figure 2:
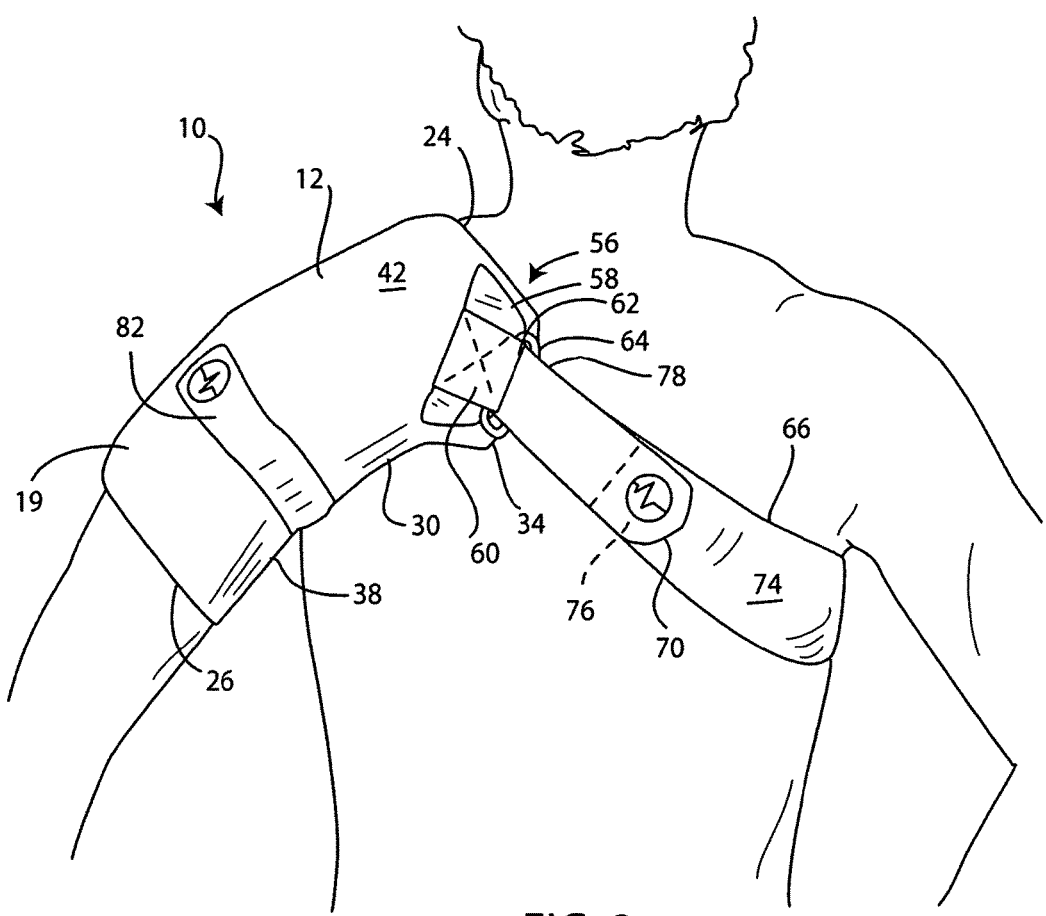
FIG. 2 is a rear view of the person wearing the shoulder wrap.
Figure 3:
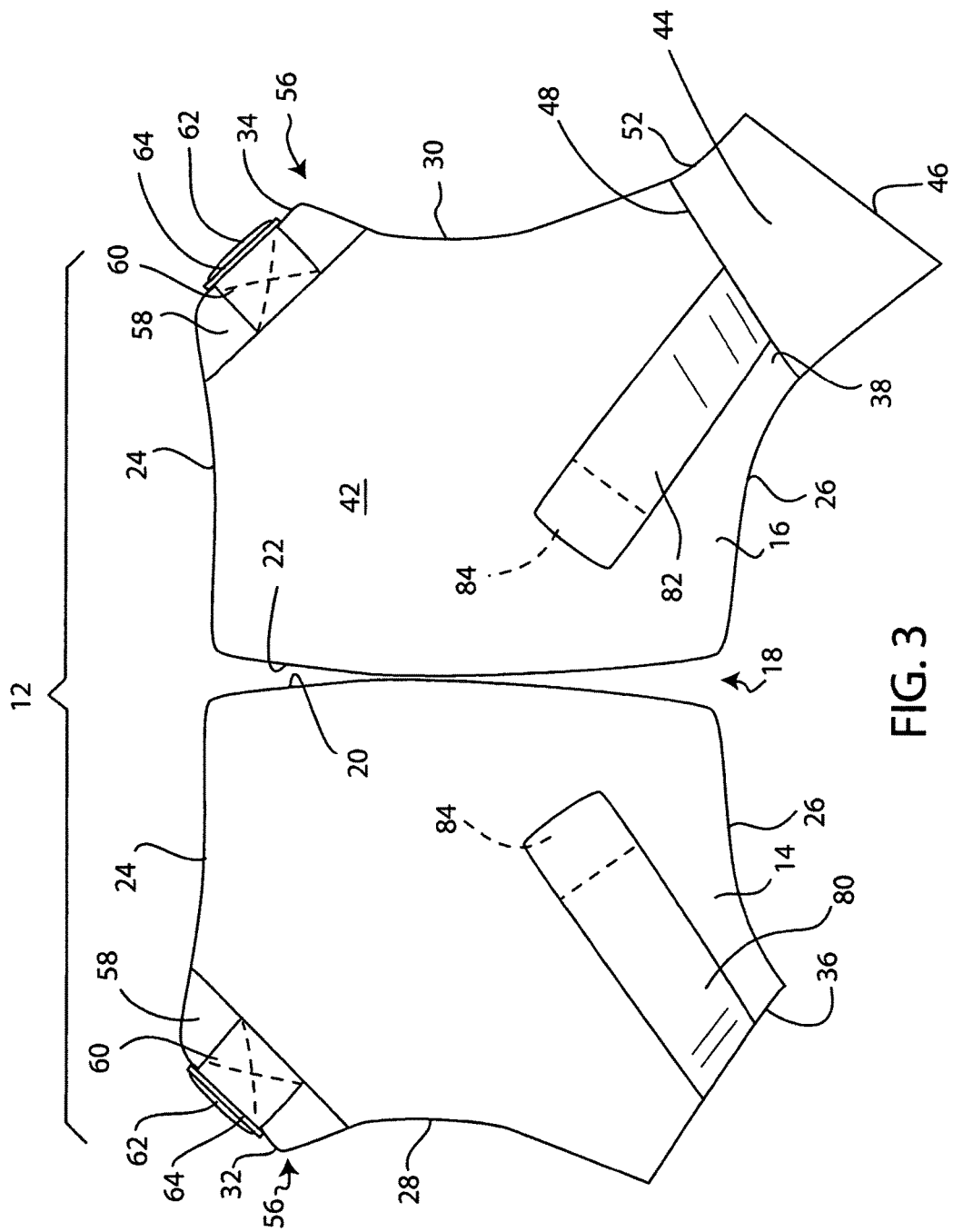
FIG. 3 is a developed view showing main panel components of the wrap laid flat, and illustrating a preferred manner of construction. This view shows exterior sides of the panel components.
Figure 4:
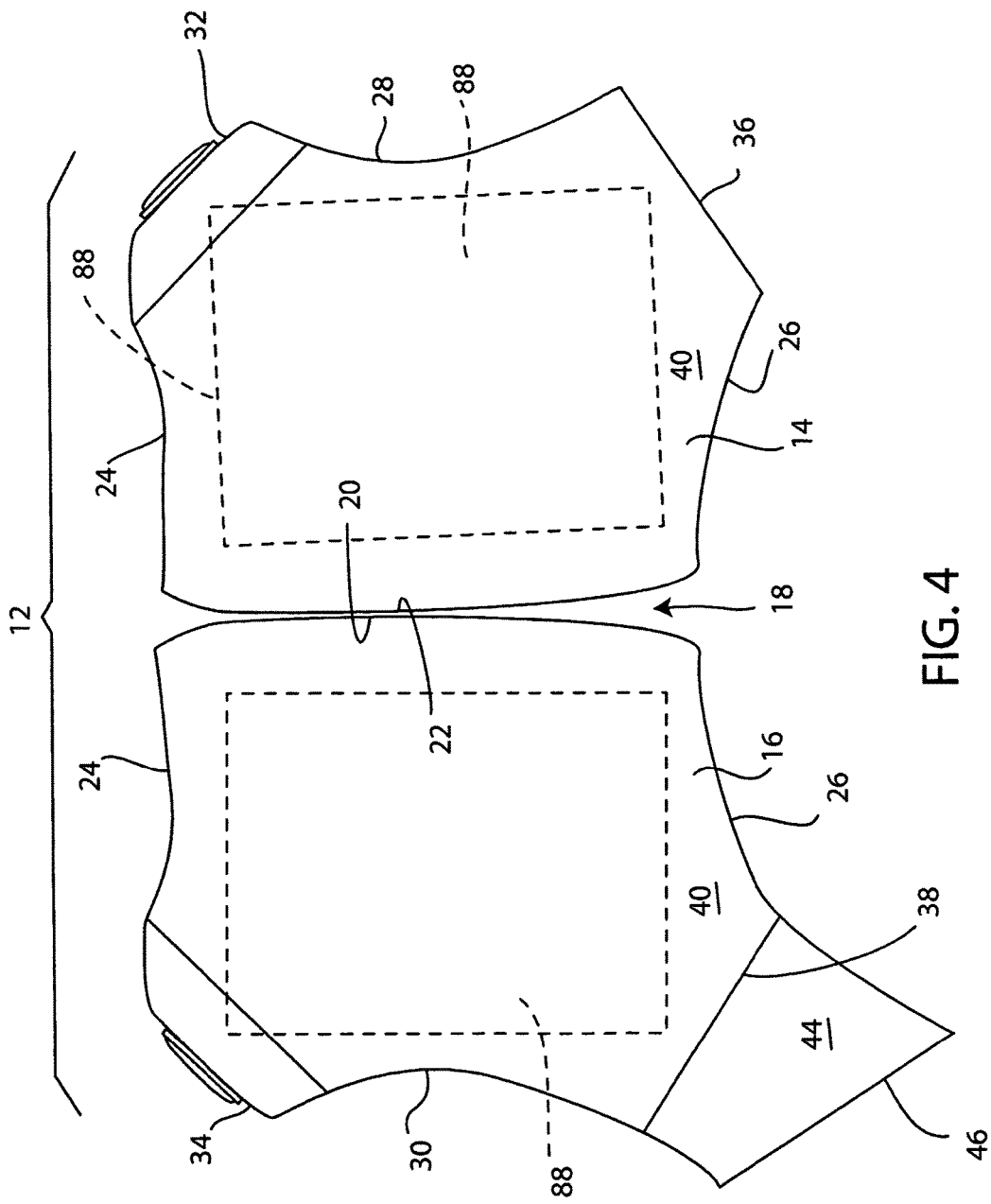
FIG. 4 is a developed view similar to FIG. 3, showing main panel components laid flat, in this case depicting the interior sides of the panel components, with pockets for gel packs.
Figure 5:
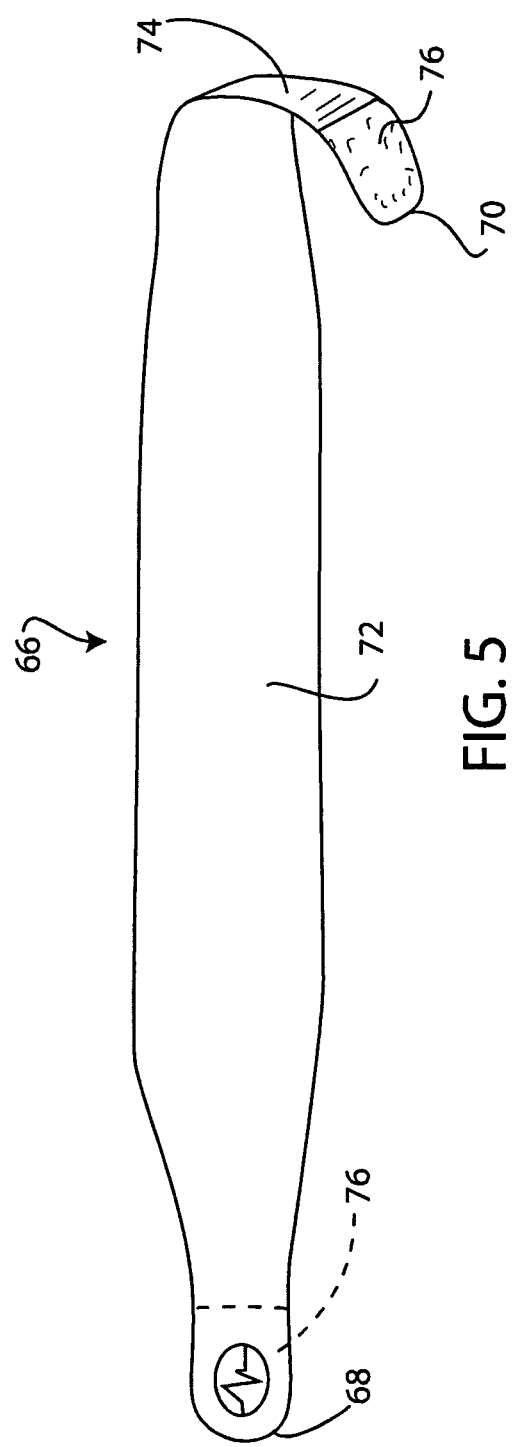
FIG. 5 shows a torso strap of the shoulder wrap.

FIGS. 1 and 2 show a thermal treatment and compression wrap 10 worn on the shoulder of a person 11 receiving treatment. As illustrated in FIGS. 1 through 5, the support includes a main or primary panel 12 formed in a concave shape from front and back portions which are shown as two panel components 14 and 16 joined at a medial seam 18. The panel components can be similarly shaped and symmetrical to one another as seen in FIGS. 3 and 4. An arm cuff 19 is formed at a lower edge of the wrap. The seam 18 secures the panels together at convex edges 20 and 22 of the components, producing the concave configuration of the main panel. The main panel has an upper edge 24 that is curved so as to conform to the panel's concavity, a curving lower edge 26 to form the arm cuff, and preferably inwardly curving side edges 28 and 30. Between the upper edge 24 and the side edges 28 and 30 the corners of the panel are truncated to provide edges 32 and 34 respectively. Similarly, the corners between the lower edge 26 and the side edges 28 and 30 are truncated to provide edges 36 and 38, part of the cuff construction.

The main panel 12 is formed from a preferably elastic sheet material which can be neoprene, but more preferably comprises the material BIO RUBBER as noted above. This material contains a highly pure limestone with calcium carbonate content exceeding 99%, and preferably exceeding 99.7%. It has a micro cellular, honeycomb structure and can be very thin, e.g. no more than about 2 mils, and provide adequate strength. The panel preferably has inner and outer plush surfaces 40 and 42 respectively.

The wrap includes a connector panel 44, also preferably elastic, with opposite side edges 46 and 48 secured to the edges 36 and 38 to form the cuff or arm hole 19 at the lower side of the main panel 12. The upper and lower edges 52 of the connector panel can be curved to continue the curvature of the adjacent edges 28, 30 and 26. The panel 44 is shown as connected (stitched) to one panel component 30 in this developed view, but of course it is connected to be the panel components 30 and 28 to form the cuff 19. If desired this connector panel 44 can be eliminated and the two panel components can be extended lower at 36 and 38 and connected directly together. However, the seams where the panel edges 36 and 38 connect to the panel 44 provide a good location for connection of compression straps as discussed below.

Along the edges 32 and 34 the main panel is fitted with strap anchors 56. Each anchor includes a non-elastic reinforcing patch 58 extending along the respective edge and secured to the edge area by stitching. A short length of webbing 60, formed into a loop 62, is stitched to the patch 58 and carries a connecting ring 64, elongated in shape, to receive a torso strap.

The shoulder wrap 10 includes a torso strap 66 (FIG. 5, also FIGS. 1 and 2) having opposite ends 68 and 70 for engaging with the strap anchors 56. The strap is preferably of an elastic material, e.g. neoprene rubber or BIO RUBBER, preferably with plush or soft inner and outer surfaces 72 and 74. Adjacent to each of the ends 68 and 70 a tab 76 of a hook fastener (VELCRO) material is fastened to the outer surface 74. The strap ends 68 and 70 are passed through the connecting rings 64 on respective sides of the main body, of the wrap and folded over to engage the fastener tabs 76 with the plush outer surface 74, which comprises loop fastener material similar to loop VELCRO material. This forms adjustable strap loops 78 (FIGS. 1 and 2) securing the torso strap to the strap anchors 56. Note that one end of the torso strap 66, such as at the back of the person, can be permanently affixed to the main panel 12, at the location of the webbing 60. The strap adjustment could be made at the front only, if it is to be used on only one shoulder (right or left).

Compression straps 80 and 82 are secured to the wrap preferably at each of the edges 36 and 38 of the panel 12, where that panel is secured to the connector panel 44. The straps 80 and 82 extend over the outer surface of the main panel 12, under the arm as in FIGS. 1 and 2, at front and back of the shoulder. A compression strap fastener system includes a patch of hook material (VELCRO) 84 secured to each compression strap at a free end of the strap, the hook material being engageable with the plush outer (loop material) surface 42 of the main panel to secure the free end of each of the compression straps to a position on the main panel selected by the user, with the strap under tension sustained by the elasticity of the main panel 12, as well as elasticity preferably in the straps 80 and 82. This enables the user or therapist to apply pressure as needed. Not only the tension can be adjusted, but the region for pressure application can be selected by moving the position where the strap 80 or 82 engages the panel (swinging the strap orientation up or down as seen in FIG. 1 or 2).

Figure 6:
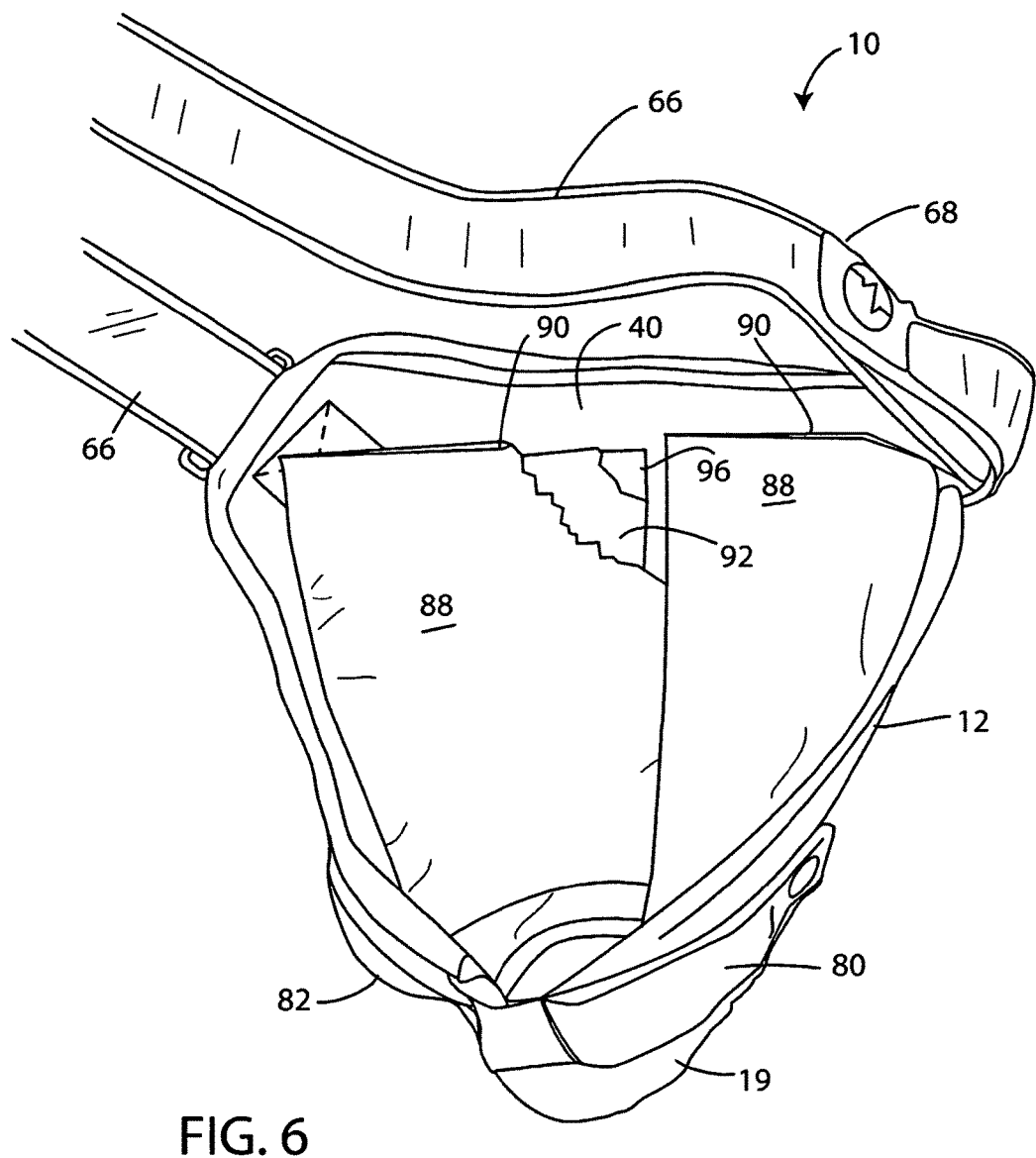
FIG. 6 is a perspective view showing the interior side of the shoulder wrap with pouches containing gel packs for thermal treatment, a pouch being partially broken away to show the gel pack.

FIG. 6 shows the assembled shoulder wrap 10 with the torso strap 66 and with the compression straps 80 and 82 secured onto the panel 12 by the hook and loop fasteners. Note that more than one strap 80 or 82 could be provided at front or back or both if desired.

The shoulder wrap also includes two textile fabric pouches 88, as shown particularly in FIG. 6, on the interior side. These are generally rectangular in shape, and each is fixed to the inner surface 40 of the main panel 12. The two pouches or pockets are dimensioned to together cover most of the inner surface of the main body 14 of the panel 12 as illustrated in FIGS. 4 and 6. The pouches extend from near the lower edge 26 to near the upper edge 24 so that in use the pouches extend over the gleno-humeral joint of the user. The pouches may extend to about one inch from each of these upper and lower edges. Each pouch has an access opening 90 at the upper end for insertion and removal of a thermal treatment medium, i.e. gel pack. In FIG. 6 one pouch or pocket 88 is broken away at a corner to show a gel pack 92.

The preferred thermal treatment medium is but not limited to a non-migrating gel pack 92. The gel packs conventionally consist of a sealed synthetic plastic envelope containing a quantity of flexible, lightweight gel material 96 which has a high heat capacity and may be either heated or chilled to provide the desired treatment. Other thermal treatment media may also be used, such as crushed ice, ice cubes or the grains that are sometimes packaged in fabric bags for use in heat treatment.

In use, the wrap 10 is prepared by placing the desired thermal treatment medium (cooled or heated) in one or both of the pouches. The arm is then inserted through the cuff 19 with the pouches positioned over the shoulder joint and the adjacent deltoid and trapezius muscle groups. The torso strap 66 is tightened by pulling at least one end through a ring 68 and fastening the strap end in place with the fastener tab 76. The front and back compression straps 80 and 82 are then oriented as desired, tightened and fastened in place to hold the treatment medium firmly against the part of the shoulder to be treated and to provide compressive support to the shoulder joint, reducing stress on the ligaments, musculature and associated tissue while allowing substantially full normal movement of the shoulder joint.

Figure 7:
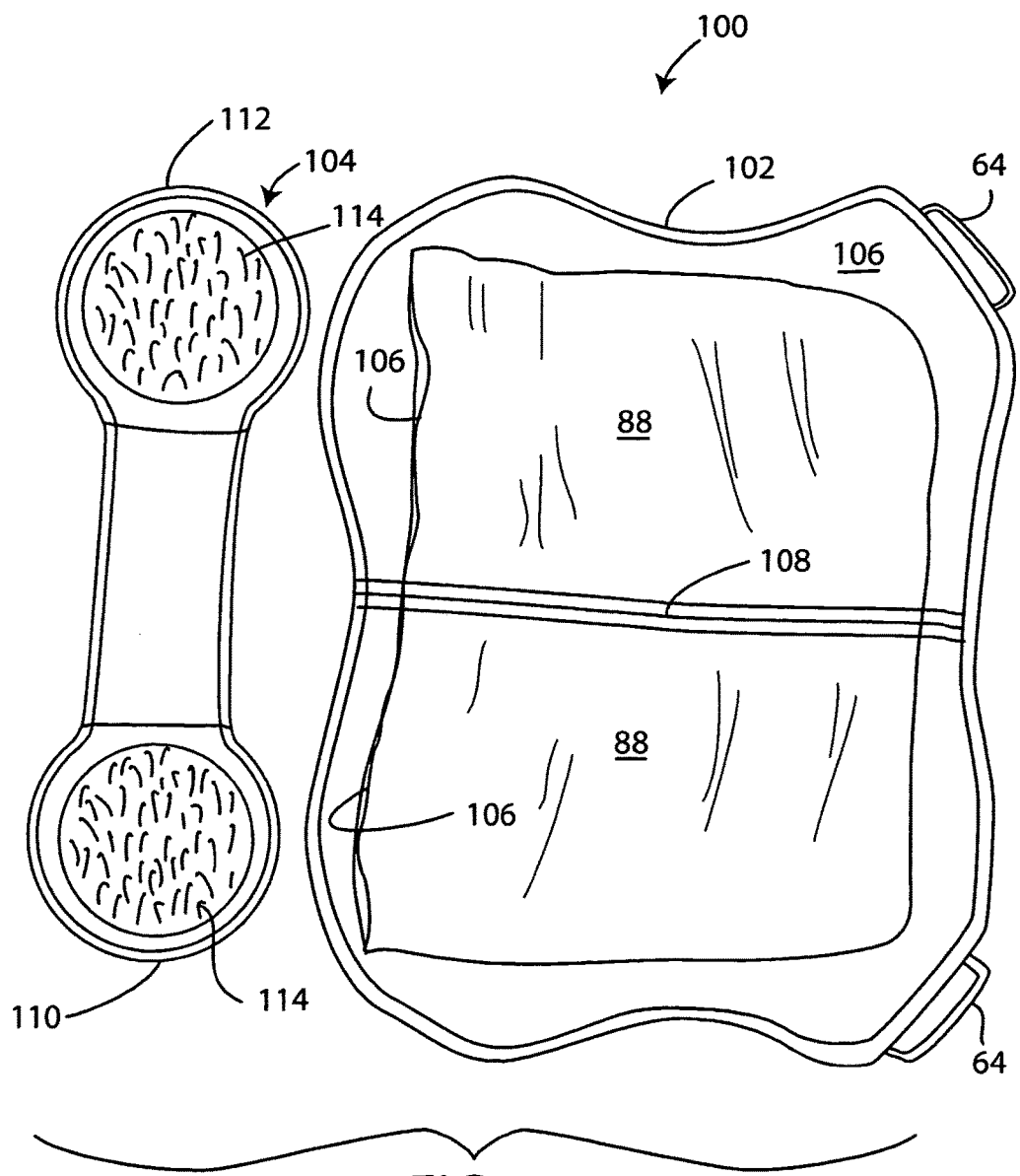
FIG. 7 is a view showing another embodiment of a shoulder wrap, without a permanently formed arm cuff, the wrap being opened and flattened. A compression strap for under arm placement is shown, but the torso strap for the wrap is not shown in this view.

FIG. 7 shows another embodiment 100 of a thermal and compression shoulder wrap of the invention. In this form the shoulder wrap has no pre-formed arm cuff. The inside of a main panel 102, along with a single compression strap 104, detached from the main panel, are shown in FIG. 7. The torso or chest strap is not shown, but it can be similar to that illustrated in the first embodiment at 66. Connecting rings 64 are seen in positions to be at front and back of the user, for receiving the chest or torso strap. As in the earlier embodiment, the strap can be permanently affixed at one of these points desired, preferably the side that would be the rear side in use. However, it is preferred that the chest strap not to be affixed to either end, so that the wrap of the invention can be used conveniently on either shoulder and adjustment can be provided at the front side. At the interior side 106 of the panel are a pair of pockets or pouches 88 for thermal gel packs. FIG. 7 shows an open end 106 at the left side of each pocket, which would be the lower side of the wrap in use, but this opening could be formed at either side, i.e. either left or right edge of the pockets 88 as seen in FIG. 7.

A central or main seam is seen at 108. This could simply be a connection for the pockets 88, and the panel 106 could be coextensive throughout the panel 102 if desired, rather than being part of two similar pieces seamed together.

In most other respects the construction of the shoulder wrap 100 can be similar to that described earlier. The outer fabric is plush or soft, and can act as loop material in a hook and loop fastening arrangement. A preferred material is BIO RUBBER, as noted above, which has a high limestone content, this allowing for a thinner wearing material that is more insulating yet more flexible than conventional products, enabling a range of motion of the user while experiencing thermal and compression therapy.

The shoulder wrap device 100 is used by inserting thermal gel packs into the pockets 88, then folding the panel 102 over the shoulder and upper arm, with the upper side having the connecting rings 64 toward the neck. Thus, one connecting ring 64 will be in front and one in back, as in the wrap shown in FIGS. 1 and 2. The chest or torso strap 66 is attached and secured as desired and may be adjusted further as needed. The compression strap 104 is then attached, under the user's arm generally similar to what is shown in FIGS. 1 and 2. The "dumbbell" shape of the compression strap 104, with large and preferably rounded ends 110 and 112, and with a large area of hook (VELCRO) material 114, enables this compression strap to be used in a very versatile manner to apply pressure in the areas needed. The ends are fully adjustable as to position and can be tightened as needed. This, in combination with the adjustment of tension in the chest strap, as well as adjustment of the position of the panel 102 itself on the shoulder, provides for very customized treatment to locate the thermal treatment and compression as needed. The length of the dumbbell-shaped compression strap may be, for example, about eleven to fourteen inches (at least about eleven inches). Its width at each end can be about three to five inches (at least about three inches).

The pockets or pouches 88 preferably are formed of a material such as nylon, which improves skin protection as opposed to net or mesh type ice holders.

In addition, the fully detachable auxiliary compression strap 104 allows for an improved pain-free fit for individuals over conventional designs. The wrap can actually be initially draped over the shoulder complex, or preset by attaching the strap 104 to the panel 102 to form an arm hole or cuff to serve as a slip-on sleeve when placed on the patient. The circular ends of the compression strap 104 provide for direct pinpoint compression to drive the cold (or heat) to precise desired areas of the shoulder region. The effect is similar to using one's opposite hand to hold ice in place.

Further, the all plush outer side (not shown) of the main panel 102 of the wrap allows the user to position the dumbbell strap 104 any where needed to apply pressure as desired. Rugged nylon backing (not specifically shown) on the panel where the buckles or connector rings 64 are located, prevents the wrap from "bunching" or "curling" when it is applied. The detachable straps, both the compression strap and the chest strap, allow for maximum size adjustment to the individual being treated.

Still further, the ergonomic design of the wrap combined with the non-migrating flex gel of the gel packs (such as used in the earlier embodiment) allows for better coverage for both hot and cold, eliminating "pooling" or "saddlebagging" which are experienced in typical water-based gel products. The cohesive gel of the gel pack molds to the shoulder unlike products with "pillow", cube or cell technology.

The adjustable chest strap secures the shoulder wrap 100 in place while providing pressure and stability in a lateral pull across the chest. This is contrasted to prior products which have simply included a strap designed to keep a wrap in place.

The described shoulder wrap 100 improves compliance, comfort and effectiveness, which greatly enhances the rehabilitation process. The device is comfortable to apply and use in any rehabilitation setting.

The invention also encompasses a particular construction and composition of thermal gel pack. This is depicted in FIGS. 8 and 9.

As shown in FIGS. 8 and 9, the thermal pack 120 adopts a double-layer construction which consists of an inner pack 122 and an outer pack 124. The inner pack is evenly segmented into small compartments 126 and filled with a kind of phase change freezing gel that has the capability to maintain at around −4° C. for several hours after frozen to be solid. The ingredient of this kind of phase change material is as shown below. Then the inner pack is inserted into the outer pack and a non-freezing cooling gel is filled in the outer pack.

A typical water-based gel pack either needs to be frozen to solid to acquire desired cold duration, or needs to be used over a shortened cold duration to keep the gel flexible after being substantially frozen. There is hardly a concurrence in a conventional water-based gel pack to remain flexible and ensure sufficiently long cold duration.

The innovation makes use of phase change technology and the above-described functional construction. The freezing point of the gel in the inner pack 122 is higher than that in the outer pack 124, so when the user freezes this combination ice pack in a household refrigerator (freezing capacity: −20° C.), gel inside the inner pack will be frozen to solid while the gel in the outer pack will still remain in a natural, flexible state because its freezing point is lower than −20° C.

After being removed from a refrigerator, the gel inside the inner pack 122 will start a phase change process which can last for many hours and release continual coldness to ensure the combination gel pack 120 to have extended cold duration. Because of the segmented construction with the inner pack and the non-freezing gel in the outer pack, the gel pack will also provide a soothing and flexible touch-feel. The gel pack 120 can remain therapeutically cold for up to four hours. In a hospital or clinic setting this greatly reduced the need for attendants.

| Ingredients of the gel in the inner pack: | |
| --- | --- |
| Sodium chloride | 0-3% |
| Potassium chloride | 0-3% |
| Ammonium hydrogen carbonate | 5-10% |
| Sodium carboxy methyl cellulose | 0.5-4% |
| Bronopol | 0.003-0.006% |
| Water | add up to 100% |

| Ingredients of the gel in the outer pack: | |
| --- | --- |
| Glycerine | 0-40% |
| Sodium chloride | 0-30% |
| Ammonium hydrogen carbonate | 0-5% |
| Sodium carboxy methyl cellulose | 0.5-4% |
| Bronopol | 0.003-0.006% |
| Water | add up to 100% |

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

I claim:

1. A therapeutic shoulder wrap for cold therapy on a human patient's shoulder and for applying pressure against the shoulder in combination with the cold, the patient having two arms, underarms, a clavicle, a chest including an upper chest, and a scapula, the shoulder wrap comprising:

a panel which is concave and configured to fit on and wrap over the shoulder so as to extend up over the clavicle and down along an upper part of an arm with a lower end of the panel formed into a cuff to encircle the upper part of the arm just below the shoulder, and the panel having front and back portions that extend down to be configured to overlap a portion of the upper chest and of the scapula, a torso strap secured to upper ends of the panel on the front and back portions, releasable at least at one end of the torso strap, and configured such that the torso strap can extend around the patient's chest and under an arm opposite to said shoulder wrapped with the panel, the torso strap being adjustable at least at one end so as to allow tension to be applied to retain the panel in place on the shoulder, a compression strap configured to be positioned at the underarm of said shoulder, with means for securing ends of the compression strap to the panel to draw the panel more tightly around the shoulder in a region of the shoulder adjacent to the underarm, and a plurality of pockets formed on an inside surface of the panel, each pocket retaining a thermal medium pack in the pocket, in a position to apply thermal therapy against the shoulder, and the thermal medium packs comprising outer packs within each of which an inner pack is contained, each inner pack being formed of a series of individual compartments, each compartment being filled with a phase-change freezing gel which after removal from refrigeration frozen solid will maintain at −4° C. for several hours and will proceed through a phase-change process over many hours, and each outer pack containing a non-freezing cooling gel surrounding each inner pack, the non-freezing cooling gel having a lower freezing point than the phase-change gel and being configured to remain flexible and pliable against the patient's shoulder, adapted to easily conform to contours of the shoulder, while containing each inner pack with frozen gel in the compartments of the inner pack, and the non-freezing cooling gel of the outer packs being non-migrating gel that independently and by its nature remains in a cohesive and integral, non-separating plastic mass, soft and with elasticity, preventing migration, pooling, separation or saddlebagging, whereby the therapeutic shoulder wrap provides for flexibility of motion of the shoulder during thermal therapy, for an extended cold duration, capable of remaining therapeutically cold for four hours.

2. The therapeutic shoulder wrap of claim 1, wherein the panel is formed of a rubbery material with limestone content, the rubbery material being no more than 2 mils thick.

3. The therapeutic shoulder wrap of claim 2, wherein the limestone has calcium carbonate content over 99%.

4. The therapeutic shoulder wrap of claim 1, wherein two said pockets are included, each formed of a smooth, thin material stitched to the inside surface of the concave panel and forming one open end to receive a said thermal medium pack in each pocket.

5. The therapeutic shoulder wrap of claim 1, wherein the torso strap has two ends and is separable from the concave panel, the panel having buckles at said upper ends of the panel to receive the ends of the torso strap, and the torso strap having hook and loop fastener material for adhering the strap at said one end to a selected point on the strap after the said one end has been passed through the buckle.

6. The therapeutic shoulder wrap of claim 1, including a permanently formed cuff or arm hole at a lower end of the panel, with two said compression straps secured to the cuff and extendable, one at each of front and back sides, up along an exterior surface of the panel to be secured to the panel using hook and loop fasteners.

7. The therapeutic shoulder wrap of claim 1, wherein the panel is essentially symmetrical such that the shoulder wrap can be worn on either shoulder.

8. The therapeutic shoulder wrap of claim 1, wherein the torso strap is completely separable from the panel, and wherein the compression strap comprises a single strap, at least eleven inches in length and having ends at least three inches wide, the single compression strap being separate from the panel and being securable to exterior surfaces of the panel, under the arm, with hook and loop fastener material.

9. The therapeutic shoulder wrap of claim 1, wherein the panel is elastic.

10. The therapeutic shoulder wrap of claim 1, wherein the torso strap is elastic.

11. The therapeutic shoulder wrap of claim 1, wherein at −20° C. the phase-change freezing gel of each inner pack is frozen solid, while the non-freezing gel in each of the outer packs is not frozen and remains in a flexible state.

12. The therapeutic shoulder wrap of claim 1, wherein the phase-change freezing gel of the inner pack includes sodium chloride, potassium chloride, ammonium hydrogen carbonate, sodium carboxy methyl cellulose, bronopol and water.

13. The therapeutic shoulder wrap of claim 1, wherein the non-freezing gel in each of the outer packs contains glycerine, sodium chloride, ammonium hydrogen carbonate, sodium carboxy methyl cellulose, bronopol and water.

14. The therapeutic shoulder wrap of claim 1, wherein the panel is of plush material acting as loop material for hook and loop fastener connections, the compression strap having hook material for engaging with the plush material.

* * * * *